United States Patent
Lapidot et al.

(10) Patent No.: US 7,150,980 B1
(45) Date of Patent: Dec. 19, 2006

(54) METHODS FOR DNA AMPLIFICATION AND SEQUENCING

(75) Inventors: Aviva Lapidot, Rehovot (IL); Robert Iakobashvili, Ashdod (IL); Gennady Malin, Boston, MA (US)

(73) Assignee: Yeda Research and Development Co. Ltd., Rehovot (IL)

( * ) Notice: Subject to any disclaimer, the term of this patent is extended or adjusted under 35 U.S.C. 154(b) by 101 days.

(21) Appl. No.: 10/117,077

(22) Filed: Apr. 8, 2002

Related U.S. Application Data

(63) Continuation of application No. 09/601,943, filed as application No. PCT/IL99/00080 on Feb. 8, 1999.

(30) Foreign Application Priority Data

Feb. 10, 1998 (IL) ..................... 123256

(51) Int. Cl.
 *C12P 19/34* (2006.01)
 *C12Q 1/68* (2006.01)
(52) U.S. Cl. .............. 435/91.1; 435/6; 435/91.2
(58) Field of Classification Search ............. 435/6, 435/91.1, 91.2
 See application file for complete search history.

(56) References Cited

U.S. PATENT DOCUMENTS

| 6,268,133 B1 | 7/2001 | Nisson et al. |
| 6,875,568 B1 | 4/2005 | Nisson et al. |

FOREIGN PATENT DOCUMENTS

| EP | 0 553 884 | 8/1993 |
| WO | 94 23055 | 10/1994 |
| WO | 95 20682 | 8/1995 |
| WO | 96 12041 | 4/1996 |
| WO | 96 34115 | 10/1996 |
| WO | 97 20949 | 6/1997 |

OTHER PUBLICATIONS

Thakar et al., "Osmolyte mediation of T7 DNA polymerase and plasmid DNA stability", BIOCHEMISTRY, vol. 33(44):12255-12259, Oct. 11, 1994.
Iakobashvili et al., "Low temperature cycled PCR protocol fr klenow fragement of DNA polymerase I in the presence of proline", Nucleic Acids Research, vol. 27 (6)1566-8, Mar. 1999.
Rajendrakumar et al., "DNA helix destabilization by proline and betaine: possible role in the salinity tolerance stress", FEBS Letters, vol. 410:210-205 (1997).

*Primary Examiner*—Jezia Riley
(74) *Attorney, Agent, or Firm*—Browdy and Neimark, PLLC

(57) ABSTRACT

The osmoprotectants proline, 2-methyl-4-carboxy-3,4,5,6-tetrahydropyrimidine ("THP(B)", and 2-methyl-4-carboxy-5-hydroxy-3,4,5,6,-tetrahydropyrimidine ("THP(A)") are capable of increasing the thermal stability of DNA polymerases at elevated temperatures. THP(B) is further effective in lowering the melting temperature of double-stranded DNA. Proline, THP(A) and THP(B) are thus useful in procedures involving melting of double-stranded DNA and/or polymerase-mediated DNA synthesis, such as in primer extension, in PCR (polymerase chain reaction) amplification and in DNA sequencing.

12 Claims, 14 Drawing Sheets

SEQUENCE LISTING

<160> NUMBER OF SEQ ID NOS: 6

<210> SEQ ID NO 1
<211> LENGTH: 12
<212> TYPE: DNA
<213> ORGANISM: Artificial Sequence
<220> FEATURE:
<223> OTHER INFORMATION: Synthetic

<400> SEQUENCE: 1

```
atgcatatgc at                                                          12

<210> SEQ ID NO 2
<211> LENGTH: 16
<212> TYPE: DNA
<213> ORGANISM: Artificial Sequence
<220> FEATURE:
<223> OTHER INFORMATION: synthetic

<400> SEQUENCE: 2
gcttaagcgc ttaagc                                                      16

<210> SEQ ID NO 3
<211> LENGTH: 28
<212> TYPE: DNA
<213> ORGANISM: Artificial Sequence
<220> FEATURE:
<223> OTHER INFORMATION: synthetic

<400> SEQUENCE: 3
cgggatccat ggaatacgta tacgctgc                                         28

<210> SEQ ID NO 4
<211> LENGTH: 28
<212> TYPE: DNA
<213> ORGANISM: Artificial Sequence
<220> FEATURE:
<223> OTHER INFORMATION: synthetic

<400> SEQUENCE: 4
cggaattctt agccgaagag ttcgccga                                         28

<210> SEQ ID NO 5
<211> LENGTH: 30
<212> TYPE: DNA
<213> ORGANISM: Artificial Sequence
<220> FEATURE:
<223> OTHER INFORMATION: synthetic

<400> SEQUENCE: 5
atggaatacg tatacgctgc actcatcctg                                       30

<210> SEQ ID NO 6
<211> LENGTH: 30
<212> TYPE: DNA
<213> ORGANISM: Artificial Sequence
<220> FEATURE:
<223> OTHER INFORMATION: synthetic

<400> SEQUENCE: 6
ttagccgaag agttcgccga ggccctcagg                                       30
```

METHODS FOR DNA AMPLIFICATION AND SEQUENCING

CROSS REFERENCE TO RELATED APPLICATION

The present application is a continuation of application Ser. No. 09/601,943, filed Aug. 10, 2000 now U.S. Pat. No. 6,428,986, which is the national stage under 35 U.S.C. 371 of PCT/IL99/00080, filed 8 Feb. 1999.

FIELD OF THE INVENTION

The present invention relates to a method for performing cycled primer extension on a DNA template, and more particularly to methods including a primer extension step such as polymerase chain reaction (PCR) amplification and nucleotide sequencing comprising performing said PCR and sequencing reactions in the presence of an osmoprotectant selected from proline, 2-methyl-4-carboxy-3,4,5,6-tetrahydropyrimidine (hereinafter "THP(B)"), 2-methyl-4-carboxy-5-hydroxy-3,4,5,6-tetrahydropyrimidine (hereinafter "THP(A)") and mixtures thereof, to improve yield and specificity of said reactions. The invention further relates to kits comprising proline, THP(B), THP(A), or mixtures thereof for use in PCR amplification and in cycle nucleotide sequencing.

BACKGROUND OF THE INVENTION

Primer extension on a DNA template is a step common to some of the most useful and powerful techniques in molecular biology. Polymerase chain reaction (PCR), one of these techniques, is a rapid, inexpensive and simple means of producing microgram amounts of DNA from minute quantities of source materials. Many variations on the basic procedure have now been described and applied to a range of disciplines.

In medicine, PCR's major impact is on the diagnosis and screening of genetic diseases and cancer, the rapid detection of mycobacteria and HIV, the detection of minimal residual disease in leukemia, and HLA typing. The PCR technique is also useful in forensic pathology and evolutionary biology, plays a central role in the human genome project and is routinely used in molecular biology processes (McPherson et al., 1992).

However, the practical use of PCR technology frequently faces difficulties and limitations. The necessity to convert originally duplex source DNA and then double-stranded DNA products into single stranded templates in every cycle of amplification is normally accomplished by thermal denaturation of DNA at 93–95° C. The DNA denaturation greatly depends on its nucleic base composition. A high GC content renders DNA amplification and sequencing very difficult, due to increased melting temperature and the stable secondary structure of the expanded motif. A common result of amplifying a region containing a repeat motif with a high GC content is the presence of additional amplification products, which do not correspond to the desired product (Varadaraj and Skinner, 1994). In addition, incomplete denaturation allows DNA strands to "snap back", leading to a decrease in product yield. Denaturation steps that are conducted for long periods of time and/or at a high temperature lead to unnecessary loss of enzyme activity and dNTP decomposition.

Taq DNA polymerase, ordinarily used in PCR protocols, can withstand repeated exposure to the high temperature (94–95° C.) required for typical DNA strand separation, and thus simplifies the PCR procedure by eliminating the need to add an enzyme in each cycle. However, Taq polymerase appears to extend a mismatched primer/template in comparison to other polymerases with proofreading exonuclease activities, e.g. Klenow and T7 DNA polymerases, which are non-thermostable.

Another very effective technique employing primer extension is the cycle sequencing technique used for determining the order of nucleic acids in a target nucleotide sequence. This procedure involves repeated cycles of primer extension while the target nucleotide sequence is sequenced.

Similar considerations, as mentioned above for the PCR method, apply for the cycle sequencing procedure. In sequencing reactions as well, the complete denaturation of the template DNA is of crucial importance for a successful reaction. Thus, regions of DNA with repeat motifs, high GC content and rigid secondary structures are difficult to sequence. In addition, sequencing of a very long stretch of nucleotides, or of a target nucleotide sequence present in a minute amount is problematic. The ability to accomplish a complete denaturation of double stranded DNA and to perform sequencing, reactions at reduced temperatures, either with Taq polymerase or with non-thermostable polymerase, is advantageous in terms of both yield and accuracy.

In an attempt to improve the yield and specificity of PCR and sequencing reactions, a number of buffer additives were employed. It was shown that certain cosolvents, such as DMSO (Pomp and Medrano, 1991; Filichkin and Gelvin, 1992), glycerol (Cheng et al., 1994; U.S. Pat. Nos. 5,432,065 and 5,545,539), formamide (Corney et al., 1991) and betaine (German Patents DE 4411594 C1 and DE 4411588 C1; Mytelka et al., 1996), facilitate standard PCR and/or cycle sequencing. It has been suggested that DMSO may affect the melting temperatures (Tm) of the template DNA and of the oligonucleotide primers and/or the degree of product strand separation at a particular "denaturation" as well as improving the thermal activity of Taq DNA polymerase (Gelfand and White, 1989). Glycerol may influence long amplifications by (i) doubling the thermal stability of Taq polymerase at 95–97° C., and (ii) effectively lowering DNA melting temperatures (by 2.5–3° C. for each 10% increase in glycerol concentration) (Cheng et al., 1994). Yet, the use of these buffer additives is limited, e.g. solutions containing glycerol in effective concentrations of 20–40% are viscous and difficult to handle (U.S. Pat. No. 5,432,065), DMSO in 10% concentration inhibits Taq DNA polymerase activity by 53% and T7 DNA polymerase is completely inactive in 40% formamide.

The compounds 2-methyl-4-carboxy-3,4,5,6-tetrahydropyrimidine [THP(B)], also known as ectoine, and its hydroxy derivative, 2-methyl-4-carboxy-5-hydroxy-3,4,5,6-tetrahydropyrimidine [THP(A)] were previously identified in the laboratory of the inventors of the present invention as metabolites in several *Streptomyces* microorganisms (Inbar and Lapidot, 1988a; 1988b and 1991; Malin and Lapidot, 1996). Ectoine was also found in a variety of halophilic and halotolerant bacteria (Galinski et al., 1985). THP(B) and THP(A) are zwitterionic compounds (Inbar et al. 1993; FIG. 1) with many useful properties such as osmoprotection and thermoprotection of several organisms of the *Streptomyces* species and *E. coli* cells (Malin and Lapidot, 1996). THP(B) and THP(A) are not toxic neither to mammalian cells nor to animals (Lapidot et al., 1995). Israel Patent No. 100810 and corresponding U.S. Pat. No. 5,789,414 and European Patent No. EP 0553884 of the present applicants disclose that THP(A) and THP(B) interact with and protect DNA in non-tumor tissues from damage by DNA-binding drugs and thus can be used for decreasing the toxic effects of DNA-binding drugs such as adriamycin and actinomycin D.

Proline is another osmoprotectant that accumulates in plants, bacteria, algae and marine invertebrates as a response to salinity stress. Proline was shown to destabilize DNA and to partially counteract the effect of sodium chloride and spermidine on the stability of the double helix, and to lower the melting temperature of DNA in a concentration-dependent manner (Rajendrakumar et al., 1997).

None of the above references describes or suggests the use of proline, THP(A) or THP(B) or mixtures thereof as additives to PCR reaction mixtures and in reactions for nucleotide sequencing.

SUMMARY OF THE INVENTION

It has now been found, according to the present invention, that THP(B) is effective in lowering the melting temperature of double-stranded DNA, and that proline, THP(B) and THP(A) are capable of increasing the thermal stability of DNA polymerases at elevated temperatures, indicating that they can be useful in procedures involving melting of double-stranded DNA and/or polymerase-mediated DNA synthesis, such as in primer extension, in PCR (polymerase chain reaction) amplification and in DNA sequencing.

Thus, in one aspect, the present invention provides a method for performing a cycled primer extension reaction comprising the steps of:

(i) contacting a template DNA comprising a target sequence of nucleotides with at least one primer oligonucleotide complementary to a nucleotide sequence at the 3'-end of said target sequence, under conditions allowing annealing of said primer to its complementary nucleotide sequence on said target sequence, in the presence of an osmoprotectant selected from proline, 2-methyl-4-carboxy-3,4,5,6-tetrahydropyrimidine [THP(B)] and mixtures thereof, to lower the melting temperature of said template DNA and/or of said primer; and (ii) carrying out a polymerase-mediated extension of said primer on said target sequence of nucleotides in the presence of an osmoprotectant selected from proline, THP(B), 2-methyl-4-carboxy-5-hydroxy-3,4,5,6-tetrahydropyrimidine [THP(A)] and mixtures thereof, to stabilize said polymerase, thus obtaining a high yield specific extension of the primer on said target sequence of nucleotides of the template DNA.

Steps (i) and (ii) may be repeated a plurality of times, for example 10–90 times, preferably 15–35 times, and each step (i) is preceded by DNA thermal denaturation at a temperature suitable for separating both said template DNA into its strands and the polymerase-extended primer of step (ii) from its complementary target sequence of nucleotides, said temperature being a temperature in which the polymerase used in step (ii) is stable.

In one embodiment, the invention relates to a method for determining a nucleotide sequence of a target DNA, wherein in step (i) the target sequence of the template DNA is a sequence of nucleotides to be sequenced, and the polymerase-mediated extension of the primer in step (ii) is carried out in the presence of all four dNTPs: dATP, dCTP, dGTP and dTTP, and in the presence of a minute amount of either ddATP, ddCTP, ddGTP or ddTTP, prior to the determination of the nucleotide sequence of the target DNA. The dGTP can be substituted by 7-deaza-dGTP described in EP 0212536.

According to this embodiment, the method for determining a nucleotide sequence of a target DNA comprises the steps of:

(i) heating a template DNA comprising a target sequence of nucleotides to be sequenced at a temperature suitable for separating said template DNA into its strands in the presence of an osmoprotectant selected from proline, 2-methyl-4-carboxy-3,4,5,6-tetra-hydropyrimidine [THP(B)] and mixtures thereof;

(ii) contacting said denatured template DNA of step (i) with a primer oligonucleotide complementary to a nucleotide sequence at the 3'-end of said target sequence of nucleotides under conditions allowing annealing of said primer to its complementary nucleotide sequence on the target sequence, in the presence of an osmoprotectant selected from proline, 2-methyl-4-carboxy-3,4,5,6-tetrahydropyrimidine [THP(B)] and mixtures thereof;

(iii) carrying out a polymerase-mediated extension of said primer of step (ii) in the presence of all four natural dNTPs: dATP, dCTP, dGTP (or 7-deaza-dGTP) and dTTP, of a minute amount of either ddATP, ddCTP, ddGTP or ddTTP and of an osmoprotectant selected from proline, THP(B), 2-methyl-4-carboxy-5-hydroxy-3,4,5,6-tetrahydropyrimidine [THP(A)] and mixtures thereof;

(iv) repeating steps (i)–(iii) a plurality of times; and (v) determining the nucleotide sequence of the target DNA.

In another embodiment, the invention provides a method for amplifying a target sequence of nucleotides by polymerase chain reaction (PCR), wherein in step (i) the target sequence of the template DNA is a sequence of nucleotides to be amplified and the template DNA is contacted with two oligonucleotide primers complementary to the nucleotide sequences at the 3'-ends of said target sequence of nucleotides and its opposite strand; in step (ii) a polymerase-mediated extension of the annealed primers of step (i) is carried out; steps (i)–(ii) are repeated a plurality of times, the last step being step (ii), thus generating multiple copies of the target sequence of nucleotides.

According to this embodiment, the invention relates to a method for amplifying a target sequence of nucleotides by polymerase chain reaction (PCR) comprising the steps of:

(i) heating a template DNA comprising a target sequence of nucleotides to be amplified at a temperature suitable for separating said template DNA into its strands in the presence of an osmoprotectant selected from proline, 2-methyl-4-carboxy-3,4,5,6-tetra-hydropyrimidine [THP(B)] and mixtures thereof;

(ii) contacting the template DNA of step (i) with two oligonucleotide primers complementary to nucleotide sequences at the 3'-ends of said target sequence of nucleotides and its opposite strand; in the presence of an osmoprotectant selected from proline, 2-methyl-4-carboxy-3,4,5,6-tetrahydropyrimidine [THP(B)] and mixtures thereof, under conditions allowing annealing of said oligonucleotide primers to their complementary sequences on said target sequence of nucleotides and its opposite strand;

(iii) carrying out a polymerase-mediated extension of the annealed primers of step (ii) in the presence of an osmoprotectant selected from proline, THP(B), 2-methyl-4-carboxy-5-hydroxy-3,4,5,6-tetrahydropyrimidine [THP(A)] and mixtures thereof; and (iv) repeating steps (i)–(iii) a plurality of times the last step being step (iii), thus generating multiple copies of the target sequence of nucleotides.

The methods of the invention are particularly useful for reactions involving GC-rich DNAs, thus diminishing or eliminating the difficulties found in amplification and sequencing of GC-rich DNA molecules. The methods are further useful for reactions involving in step (ii) or (iii) a thermostable DNA polymerase, such as Taq polymerase Klentaq1 polymerase and Pfu polymerase, or a non-thermostable DNA polymerase such as T7 DNA polymerase, T4 DNA polymerase, Klenow fragment of DNA polymerase I, reverse transcriptases, Bca polymerase, Bst polymerase and mutants of these polymerases.

In another aspect, the invention relates to the use of an osmoprotectant selected from proline, THP(B), THP(A) and mixtures thereof as an additive in a reaction for determining a nucleotide sequence or as an additive to a PCR reaction mixture, and to kits comprising in separate containers: (a) the reagents necessary for DNA sequencing or the reagents necessary for a polymerase chain reaction, and (b) proline, THP(A) or THP(B).

In a further aspect, the invention relates to a method for lowering the melting temperature of double-stranded DNA (dsDNA) comprising adding to the incubation mixture of said dsDNA an effective amount of THP(B).

In a further aspect, the invention relates to a method for increasing stability of a DNA polymerase at elevated temperatures comprising adding to the incubation mixture of said polymerase an effective amount of an osmoprotectant selected from proline, THP(B), THP(A) and mixtures thereof.

BRIEF DESCRIPTION OF THE DRAWINGS

(FIG. 7A), 90° C. (FIG. 7B) and 89° C. (FIG. 7C), in the absence and presence of 1.0M THP(B). Two or three repetitions of each experiment are shown.

FIG. 8A:— (filled diamonds)—no proline added; (open squares)—2.0M; (filled triangles)—3.5M; (filled squares)—5.0M; (open triangles)—5.5 M; (filled circles)—6.2M proline. FIG. 8B, in the presence of 6.2 M proline; (open triangles)—*Micrococcus lysodeikticus* DNA; (filled triangles)—*Clostridium perfringens* DNA: (filled squares)—calf thymus DNA; (filled circles)—poly(dA-dT).

DETAILED DESCRIPTION OF THE INVENTION

Figure 1:
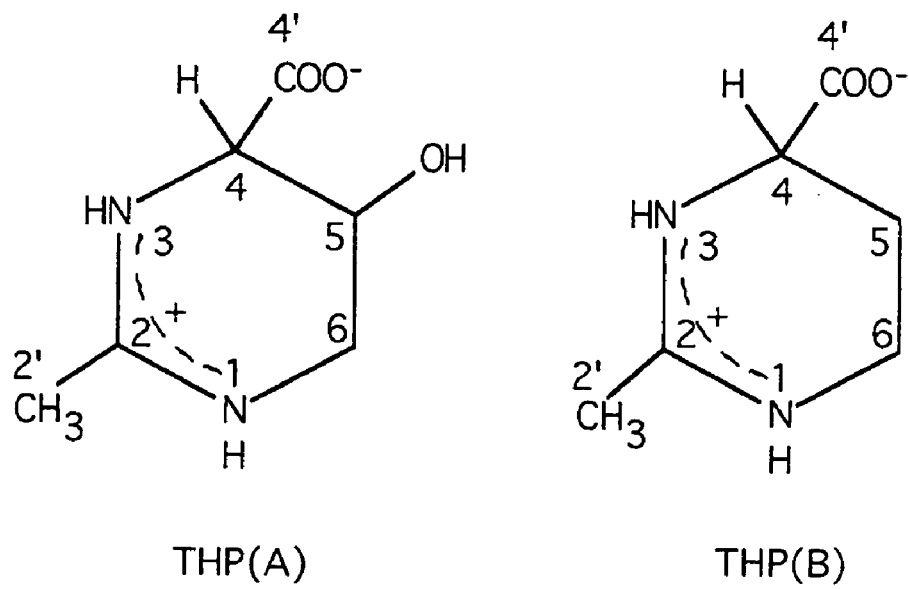
FIG. 1 depicts the structural formulas of THP(A) (left) and THP(B) (right).

The term "primer extension" as used herein in the specification refers to a process of increasing the length of an oligonucleotide complementary to a nucleotide sequence comprised within a template DNA. The process consists of repeatedly adding to the oligonucleotide's 3'-end a single nucleotide which is dictated by the nucleotide present at the corresponding position in the complementary template DNA strand. The term "cycled primer extension" refers to a procedure which involves repeated cycles in which primer extension is alternated with periodic heating whereby separation of the extended primer from the template DNA strand occurs.

The term "melting temperature (Tm)" of double-stranded DNA (dsDNA) refers to a temperature at which 50% of a dsDNA sample is separated into its two complementary DNA strands.

The term "amplifying" refers to repeated copying of a specified sequence of nucleotides resulting in an increase in the amount of said specified sequence of nucleotides.

The term "sequencing" refers to a procedure for determining the order in which nucleotides occur in a target nucleotide sequence.

The term "target nucleotide sequence" refers to a nucleotide sequence which is intended to be duplicated, amplified or sequenced.

The term "template DNA" refers to DNA molecules or fragments thereof of any source or nucleotide composition, that comprise a target nucleotide sequence as defined above.

According to the present invention, THP(B) or proline or mixtures thereof can significantly lower the melting temperature of dsDNA, and proline, THP(B) or THP(A), alone or in combination, increase the stability of DNA polymerases incubated at elevated temperatures.

THP(B) and THP(A) for use in the invention can be isolated from natural sources such as, for example, from actinomycin D-producing microorganisms of the *Streptomyces* species, e.g. *S. parvulus*, *S. chrismomalus*, or *S. antibioticus*, and separated in purified form as described in IL Patent No. 100810 and corresponding U.S. Pat. No. 5,789,414 and EP 0553884. THP(B) alone can be isolated and purified from halophilic and halotolerant bacteria such as bacteria of the genus *Ectothiorhodospira*, e.g. *E. halochloris*, *E. halophila* and mutants thereof or from heterotrophic halophilic eubacteria of the family Halomonadaceae grown in high salinity conditions. THP(A) alone can be isolated and purified from soil microorganisms of the *Streptomyces* species, e.g. *S. clavuligerus*, *S. griseus* and mutants thereof, under low salt stress such as 0.25–0.5M NaCl. THP(B) can also be synthetically produced as described in Japanese Patent Application No. 63-259827.

L-Proline is a common amino acid that is commercially available or can be synthetically produced and obtained in highly purified form.

According to the invention, THP(B) was found to decrease the Tm of oligonucleotides as short as 6–8 mers and of dsDNAs being either genomic DNAs, cDNAs or recombinant DNA molecules, in a concentration dependent manner in concentrations ranging from 0.5 to 4M. The melting temperature of short oligonucleotides (6 or 8 mers) were reduced by 3 to 6° C. in the presence of 0.5M and 1.0 M THP(B).

The magnitude of the Tm decrease depends on the GC content of the particular oligonucleotide or dsDNA, being more pronounced with high GC content DNAs. For example, the Tm decrease of calf thymus DNA (42% GC) and of *Micrococcus lysodeikticus* DNA (72% GC content) in the presence of THP(B) was significantly higher than that of *Clostridium perfringens* DNA (26% GC content), while no change in the Tm of the synthetic oligonucleotide poly(dA-dT) could be observed in the presence of THP(B) at concentrations as high as 4M. At 4.0 M concentration of THP(B), DNAs with different GC content melt in a very narrow temperature range (40–43° C.), while in the absence of THP(B) the melting temperature ranges from 39 to 75° C. Isostabilization of the DNA molecule by THP(B) may be explained as a result of greater destabilization of GC-rich than AT-rich DNAs. THP(B) eliminates the DNAs base pair composition-dependence on DNA melting.

Proline, known to decrease DNA melting temperature (Rajendrakumar et al., 1997), was found according to the invention to only slightly decrease Klenow polymerase enzymatic activity and to be a better stabilizer of Klenow polymerase than glycerol, with a half-life of the enzyme of 21 min at 65° C. in 5 M L-proline. These findings have enabled a successful design of a PCR protocol for a rather GC-rich genomic DNA template. The amount of Klenow polymerase in the herein presented protocol (10–15 units) can be further reduced when 7-deaza-dGTP is used instead of dGTP, due to the expected decrease of denaturation temperature. The results herein reveal that proline concentration in the range of 3–5.5 M is sufficient to confer stability to Klenow polymerase.

Proline can be used as a sole additive in the protocol or in combination with glycerol or any other DNA-destabilizing agent which the polymerase tolerates, such as THP(B) or THP(A). Proline (up to 5.0 M) decreases the melting temperature (Tm) of various DNAs and leads to DNA partial "isostabilization" (a decrease of Tm difference between GC and AT pairs, manifested by an apparent linear decrease of dTm/dGC factor (Melchior et al., 1973; Rees et al., 1993), while at higher concentrations, proline destabilizes GC and AT pairs evenly. A complete "isostabilation" of DNA, as in the case of betane (Rees et al., 1993) THP(B) (equal stability of AT and GC pairs, dTm/dGC=0), was not reached for proline. The Tm values of the tested natural DNAs (57–78° C.) decreased to a narrow range of 28–32° C. in the presence of 6.2 M prolione. The partial "isostabilization" of DNA by proline at high concentration may cause low specificity of PCR, when 20–25 b.p. primers are used.

Primers of 30–35 b.p. length, used in the herein presented PCR protocol, were found to be effective to remedy the decreased priming specificity at high concentrations of proline, and to achieve a good selectivity of amplification.

Besides standard PCR and DNA sequencing, the protocol with proline can be interesting for the following methods: a) use of Klenow polymerase in combination with contiguous hexamer primers and single-stranded DNA binding protein for a specific primer formation (Kieleczawa et al., 1992) utilizing a rather low amount of a source DNA; b) low denaturation temperature cycling might enable usage of less thermostable labels for DNA sequencing or PCR. This approach might be useful for other thermolabile polymerases in PCR and other DNA amplification methods. For example, T7 DNA polymerase and its modifications, able to amplify GC-rich DNA and regions with stable secondary structures, could provide solutions to the cases still remaining beyond today's practical PCR and DNA sequencing capabilities, such as amplification of long CGG triplet repeat sequences. Introduction of T4 polymerase to cycled PCR might be of interest for the cases requiring high fidelity, e.g. for amplification of sequences present at a very low frequency requiring many cycles of amplification to be detected.

According to the invention it was further found that proline, THP(B) and THP(A), alone or in combination, can stabilize both thermostable and non-thermostable DNA polymerases incubated at elevated temperatures, the stabilizing effect being more pronounced when the enzyme is incubated for prolonged periods of time and at a higher temperature than the temperature of their optimal activities. The thermostable Taq polymerase, after 30–35 min incubation under typical DNA denaturation temperature at 95° C., is only 50% active, and after 30 min incubation at 97° C., only 10% active in comparison to 40% in the presence of 1M THP(B) and even higher, 55%, in the presence of THP(A). A much more dramatic effect is obtained at longer incubation time (60 min), where the remaining activity is less than 5% without additives and is 55% in the presence of THP(A) (by 10-fold higher). The non-thermostable polymerases are much more sensitive to thermal inactivation, for example, the half life of Klenow DNA polymerase is around 30–50 seconds at 65° C., whereas in the presence of 5M proline it is 25 min, about 30–50 fold longer.

In preferred embodiments, cycled primer extension of any template DNA is conducted with the thermostable Taq polymerase at 60–80° C. in the presence of 0.5–3.5M THP(B), optionally with 0.5–3.0M THP(A), or 1–5M proline, or with a non-thermostable polymerase at 30–65° C. in the presence of 1–3 M THP(B), optionally with 0.5–3.0M THP(A), or 1–5M proline.

Lowering the Tm of dsDNA by proline and/or THP(B) and stabilization of DNA polymerases by proline, THP(B) and/or THP(A) are beneficial for cycled primer extension procedures that comprise steps of DNA melting and of polymerase-mediated DNA synthesis, such as DNA sequencing and PCR procedures, leading to high yields of dsDNA denaturation, namely separation of dsDNA into its two complementary strands at a lower temperature, and high performance of DNA polymerases.

The concentration of the osmoprotectant to be used in a particular cycled primer extension reaction depends on the specific template DNA, the primer(s), the DNA polymerase and the reaction conditions employed. Low concentrations of THP(B) or proline, typically around 0.5–1.5M, are preferred for lowering Tm of an average GC-content DNA, while higher concentrations, typically 1–3M, are preferred for high GC-content DNA, so to further lower the Tm and hence the denaturing temperature employed. To avoid major dissociation of primer/template DNA, when high concentrations of THP(B) (3–4M) and proline (4–5M) are used to lower DNA Tm to the range of 40–55° C., primers of at least 30 nucleotides are used. These modifications improve annealing and yield of the reaction.

The use of non-thermostable DNA polymerases such as T7 DNA polymerase or Klenow is of major importance in cases where accuracy of DNA amplification is crucial such as in detection of subtle changes in a DNA sequence and in processes of PCR typing and diagnosis of some genetic diseases and cancer caused by minor mutations, due to their high fidelity in DNA replication and proofreading ability.

Performing primer extension reactions at reduced temperatures also permits the use of thermosensitive fluorescent and other labile compounds for labeling newly synthesized DNA strands for use as probes in the detection of complementary target sequences of nucleotides by sensitive assays such as, chemiluminescence detection.

Reaction conditions used in PCR are variable depending on the nature of the template DNA and primers, and optimal pH and salt and magnesium ions concentrations are usually determined empirically for each particular reaction. A typical PCR procedure involves temperature cycling to provide adequate conditions for accomplishing three steps in each PCR cycle: (i) DNA denaturation; (ii) primer annealing; and (iii) primer extension.

A standard denaturation incubation step (i) at 94–95° C. for 0.5–2 min is usually sufficient for separating DNA strands of an average GC content from the original and newly synthesized DNA. The primer annealing step (ii) is performed usually around 5° C. lower than the melting temperature of the primer-template DNA duplex. However, if non-specific PCR products are obtained in addition to the expected product, the annealing temperature should be increased. The extension (step iii) of the annealed primer at its 3' end to synthesize a new DNA strand, complementary to the template strand, is usually carried out by the thermostable enzyme Taq polymerase at 70–75° C., which is the optimal temperature range for the enzyme activity (~2–4 Kb/min.).

The complete denaturation of the DNA template, especially at the first amplification cycles, is of most importance in PCR procedures, otherwise its use as a template for the following reaction steps decreases and results in poor yield of the PCR product. This is especially relevant when an amplified DNA duplex has a very high GC content, rendering it difficult in strand separation, or when a target nucleotide sequence is present in a minute amount in the initial reaction mixture. Thus, PCR buffers containing solutes leading to significant lower Tms of the DNA templates are most important in PCR procedures. The addition of proline THP(B), THP(A) or mixtures thereof to PCR procedures is beneficial in three levels: (i) increased yield of the amplified DNA products; (ii) increased sensitivity and (iii) increased specificity of the reaction. The effect of proline and THP(B) in decreasing Tms of oligonucleotide primers and of template DNAs, and the effect of proline, THP(B) and THP(A) in stabilizing DNA polymerases, result in more efficient use of the template DNAs, primers and enzymes of the reaction, leading to high yield of PCR-amplified DNA product. Moreover, the increased sensitivity of PCR assays in the presence of the additive enables detection of target DNA sequences that are not detectable in its absence. This is especially significant in cases where very rare or long target sequences are to be amplified. In addition, the additives also improve the quality of PCR amplification by reducing significantly or eliminating nonspecific products. The improved accuracy of PCR in the presence of proline, THP(B) and/or THP(A) enables performing PCR protocols with increased number of cycles and longer cycle times, without impairing the quality of the reaction products.

In another embodiment, the invention provides a method for cycle DNA sequencing comprising contacting a template DNA with a primer homologous to a specific sequence on a target DNA in the presence of a DNA polymerase and an effective amount of proline, THP(B) and/or THP(A) under conditions allowing DNA sequencing.

A commonly used cycle DNA sequencing protocol known as Sanger or dideoxy sequencing method, typically includes isolating double stranded template DNA, separating it into its component single strands, adding a sequencing primer homologous to a sequence of nucleotides on the target DNA and performing a cycled primer extension of said primer on the target DNA. The cycled primer extension is performed in four paralleled reactions, each including a small amount of a dideoxynucleotide triphosphate, either ddATP, ddCTP, ddGTP or ddTTP, along with a molar excess of the four deoxynucleotide triphosphates (dNTPs) normally required for DNA synthesis, i.e. dATP, dCTP, dGTP or dTTP. The growth of the extended DNA chain is stopped once a ddNTP molecule is incorporated into it, thus generating series of extension products of various lengths. When these extension products of the four extension reactions are separated side by side, for example on a polyacrylamide gel, a pattern is obtained. By using a labeled primer or labeled ddNTP, typically radioactive or fluorescent, this pattern can be monitored, for example, by autoradiography, fluorescence detectors etc, and the DNA sequence can be determined.

Cycle DNA sequencing also involves cycle primer extension, thus the sequencing outcome is influenced by similar criteria as mentioned above for PCR. The degree of template DNA and primer denaturation, as well as the polymerase performance, are of crucial importance for the sensitivity and accuracy of a sequencing reaction. The exact reaction conditions for performing a cycle DNA sequencing method and the effective concentrations of the added osmoprotectant vary depending on the template DNA, primers, target DNA to be sequenced and the DNA polymerase used in a particular reaction.

Cycle sequencing performed in accordance with the invention in the presence of proline, THP(B) and/or THP (A), is a beneficial and sensitive tool. The osmoprotectant additive permits obtaining a sequence of a longer stretch of nucleotides in a single reaction, as well as to sequence minute amounts of DNA present, for example, in limited samples of blood or tissue used in forensic pathology and in evolutionary biology. In addition, some GC-rich DNAs or other DNAs with complex or rigid secondary structure that are very difficult to sequence using conventional reaction mixtures, can thus be successfully sequenced. Since in the presence of the additives the specificity of primer annealing is increased and non-specific extended products are mostly eliminated, detection of rare mutations becomes feasible. This is especially important in diagnosis of diseases characterized by a small mutation in a gene nucleotide sequence or in identification of high CGG repeats that are indicative of many human disorders, such as Huntington's disease (Han et al., 1994).

The kits for performing DNA amplification by PCR or for DNA cycle sequencing of the invention include, respectively, the reagents necessary for PCR or DNA sequencing (e.g. appropriate buffers, dNTPs, either Taq or a non-thermostable polymerase, etc.) and, in separate containers, THP(B) optionally with THP(A) or proline.

Examples

Materials and Methods (i) Materials

For Examples 1–4, THP(A) and THP(B) were prepared according to Malin and Lapidot (1996) and their water solutions were passed through a chelex column to remove divalent cations before use. Betaine (Sigma) was dissolved in water and passed through a chelex column before use. Taq DNA polymerase (recombinant) and Klenow fragment of DNA polymerase I (10 units/µl) were purchased from MBI Fermentas, calf thymus DNA (used in the DNA melting examples) and activated calf thymus DNA (used in the polymerase activity assays), *Micrococcus lysodeikticus* DNA, *Colstridium perfringens* DNA and poly(dA-dT) from Sigma. The oligonucleotides [d(ATGCAT)]$_2$ (SEQ ID NO:1) and [d (GCTTAAGC)]$_2$ (SEQ ID NO:2) and the following 28-mer primers 1 and 2 were prepared by solid-phase phosphouramidate synthesis:

1. 5'>CGG GAT CCA TGG AAT ACG TAT ACG CTG C<3'(SEQ ID NO:3)

2. 5'>CGG AAT TCT TAG CCG AAG AGT TCG CCG A<3'(SEQ ID NO:4)

For Examples 5–9, L-proline 99+% and 99.5+% were purchased from Sigma and from Fluka, respectively, and glycerol was from BDH. Activated calf thymus DNA and calf thymus DNA was from Sigma. Taq DNA polymerase (recombinant) and Klenow fragment of DNA polymerase I (10 units/µl) were purchased from MBI Fermentas. Klentaq1 DNA polymerase from AB Peptides and Pfu DNA polymerase (cloned) from Stratagene. *Halobacterium marismortui* genomic DNA template was a generous gift of Dr. Shulamith Weinstein (Kimmelman Laboratory of Biocrystallization, Weizmann Institute of Science).

Two pairs of primers were used in Examples 7–9: two 28-mer primers 3 and 4 with 22 of complementary nucleotides each and with end restriction site: primer 3 containing BamHI restriction site and primer 4 containing EcoRI restriction site, and two 30-mer primers 5 and 6 with all 30 complementary nucleotides:

3. 5'>CGG GAT CCA TGG AAT ACG TAT ACG CTG C<3' (SEQ ID NO:3)

4. 5'>CGG AAT TCT TAG CCG AAG AGT TCG CCG A<3' (SEQ ID NO:4)

5. 5'>ATG GAA TAC GTA TAC GCT GCA CTC ATC CTG<3'(SEQ ID NO:5)

6. 5'>TTA GCC GAA GAG TTC GCC GAG GCC CTC ACC<3' (SEQ ID NO:6)

All oligonucleotides and primers for Examples 1–9 were prepared by the Chemical Service Unit of the Weizmann Institute of Science, Rehovot, Israel, and their solution concentrations were determined by UV absorbance at 260 nm.

(ii) DNA Melting Experiments

DNA melting studies were conducted in a buffer (1 ml) containing 5.0 mM K$_2$HPO$_4$ and 0.1 mM Na$_2$EDTA at pH 7.5. The buffer and THP(B) or pro line solutions were filtered through 0.22 µm Millipore membrane filter, prior to addition of the DNA, and then degassed with helium at room temperature. DNA samples were adjusted to O.D.$_{260}$=0.2 and incubated overnight at 37° C. before use, as previously described (Rees et al., 1993). DNAs in the above buffer with and without THP(B) or proline were measured in 1-cm path Teflon-stoppered quartz cell and incubated at the initial assay temperature for 5 min. The increase in absorbance at 260 nm was monitored in Hewlett Packard 9450A diode array spectrophotometer attached to a temperature programmer and controller. Both the sample and the reference cells were heated together at a rate of 0.5° C./min and the net absorbance was recorded after every 0.5° C. increase. The Tms were determined graphically from the midpoints of the absorbance versus temperature profile.

(iii) NMR Measurements of Chemical Shift Changes $^1$H NMR measurements were carried out on a Bruker AMX 400 NMR MHZ spectrometer at 400.13 MHZ (equipped with an Aspect 300 control). For the $^1$H NMR measurements, 1.0 mM DNA oligonucleotides were dissolved in 0.5 ml phosphate buffer solution (pH 7.2) in $D_2O$ (20 mM, for [d(ATGCAT)]$_2$ (SEQ ID NO:1) and 40 mM for [d(GCTTAAGC)]$_2$ (SEQ ID NO:2) containing 50 mM NaCl and 0.1 mM EDTA. The solutions were lyophilized and then redissolved in 0.5 ml $D_2O$ (99.96%), heated to 65° C. and gradually cooled to 5° C., and then degassed with argon at room temperature.

(iv) Klenow DNA Polymerase Activity Assay

The assay was performed at 37° C. in 15 μl reaction mixture containing 67 mM Tris-HCl (pH 7.4), 1.0 mM β-mercaptoethanol, 5.2 nM [α-$^{32}$P]dATP, 6.41 μM dATP and 320 μM of each dCTP, dGTP, dTTP, 0.6 mM activated calf thymus DNA, and 6.7 mM $MgCl_2$ for THP or 6.7, 10.0 and 15 mM $MgCl_2$ for proline. Klenow fragment (0.1 units) was added to the microtubes with reaction mixture preheated to 37° C., and following 7.5 minutes incubation at 37° C. (a time-point within the region of linear kinetics determined in a separate experiment, not shown), the reaction microtubes were placed on ice, and the reaction was stopped by addition of 12 μl of 50 mM EDTA and then applied on strips of chromatographic paper (Whatman No. 3). Strips were washed three times by cold TCA 10%, dried and the radioactivity was counted.

(v) Determination of Remaining Activities of Taq Polymerase after Incubation with THP(A) or THP(B) at Elevated Temperatures Taq polymerase (0.5 units) was added to 50 μl buffer containing: 10 mM Tris-HCl (pH 8.8 at 25° C.), 2.5 ng Halobacterium marismortui genomic DNA template, 2 μM of each of the dNTPs: dATP, dCTP, dGTP and dTTP, 0.12 nM of each of the two 28-mer oligonucleotide primers 1 and 2 described in section (i) above, 50 mM KCl, 0.08% Nonidet P40 and 1.0 mM $MgCl_2$. THP(B), THP(A) or glycerol were added from 3M stock solutions (pH 8.8 at 25° C.). The reaction mixtures were overlaid with paraffin oil and incubated at 95° C. or 97° C. Aliquotes (7.5 μl) were taken for polymerase activity assay at different periods of time.

Figure 11:
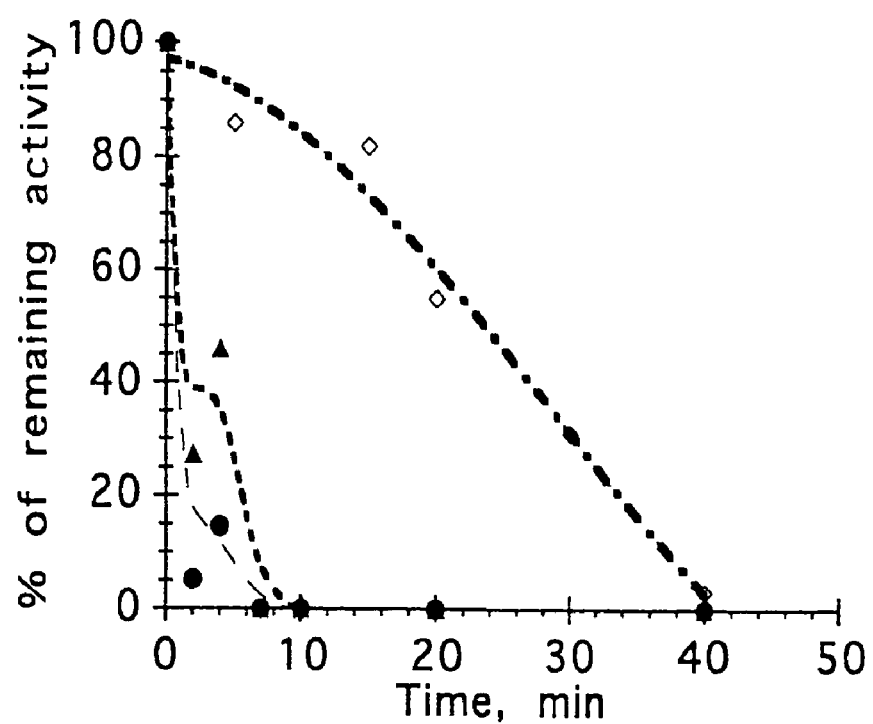
FIG. 11 depicts the time course of thermal inactivation of Klenow DNA polymerase at 65° C. in the absence (filled circles) and presence of either 5M proline (open diamonds) or 5M glycerol (filled triangles). The remaining activity of Klenow DNA polymerase was measured at different periods of time as described in Materials and Methods, section (vii).

(vi) Determination of Remaining Activity of Klenow DNA Polymerase after Incubation at 65° C. with Proline Klenow DNA polymerase (0.5 unit) was incubated at 65° C. in 50 ml buffer containing: 67 mM Tris-HCl (pH 7.4 at 25° C.), 2.5 ng Halobacterium marismortui genomic DNA template, 4 μM of each of the dNTPs: dATP, dCTP, dGTP and dTTP, 0.12 nM each of the two 28-mer oligonucleotide primers 3 and 4 described in section (i) above, 6.7 mM $MgCl_2$ and either without or in the presence of 5.0M glycerol or proline. Tris-HCl buffer, template DNA, dNTP, primers and $MgCl_2$ were added to PCR microtubes, evaporated to dryness by speed-vacuum and respective volumes of water, proline (from a 5.5M stock solution) or glycerol (from a 5.5M stock solution) were added. The microtubes were vortexed and Klenow enzyme was added to the samples. Aliquots (5 μl) were taken for polymerase activity assay at different periods of time as indicated in FIG. 11. The Klenow DNA polymerase activity assay was performed as described in section (iv) above at 6.7 mM concentration of $MgCl_2$. To each aliquot (5 μl) 20 μl of stock solution containing all other components of the assay were added, making a total reaction volume of 25 μl and a 5-fold dilution of the aliquots. Thus, proline and glycerol concentrations in the polymerase assay were 1.0M, shown to be stimulative for Klenow polymerase activity in a separate experiment (data not shown).

(vii) Polymerase Chain Reaction (PCR) Procedure with THP(B)

PCR was performed in 25 μl reaction mixture containing 3 ng template DNA, 0.12 nM of each 28-mer oligonucleotide primer 1 and 2 described in section (i) above, 0.5 units Taq DNA polymerase, 200 μM of each dNTP, in PCR buffer containing: 10 mM Tris-HCl (pH 8.8 at 25° C.), 50 mM KCl, 0.08% Nonidet P40. $MgCl_2$ concentrations of 1.0 mM and 1.75 mM were used in the absence and presence of THP(B), respectively, added from a 3M stock solution (pH 8.8 at 25° C.). Reaction mixtures were overlaid with paraffin oil and preheated for min at their respective denaturing temperatures except for mixtures of reactions performed at Td 95° C., that were preheated for 3 min at 94° C., and then subjected to 35 thermal cycles as follows: (i) 30 sec incubation at 89–95° C., as indicated in each experiment (denaturation step); (ii) 90 see incubation at 55° C. (annealing step); and (iii) 60 sec incubation at 72° C. (primer extension).

(viii) PCR in the Presence of Proline, Using Klenow DNA Polymerase.

PCR was performed in a 25 μl reaction mixture containing 100 ng Halobacterium marismortui genomic DNA template, 0.12 nM of each 30-mer oligonucleotide primers 5 and 6 described in section (i) above, 10 or 15 units of Klenow DNA polymerase, 0.9 mM of each dNTP, in PCR buffer containing: 10 mM Tris-HCl (pH 7.4 at 25° C.) and 15 mM $Mg(OAc)_2$. Tris-HCl buffer, template DNA, dNTP, primers and $Mg(OAc)_2$ were added to PCR microtubes, evaporated to dryness by speed-vacuum and dissolved in 22 μl of a proline-glycerol solution (5.5M of L-proline in 12.5% w/v solution of glycerol in water). Reaction mixtures were preheated for 3 min at 75° C., and then subjected to 35 thermal cycles as follows: (i) 20 sec incubation at 70° C. (denaturation step); (ii) 4 min incubation at 37° C. (primer annealing and primer extension steps). Klenow DNA polymerase (10 or 15 units) diluted up to 3 μl volume, containing 50% w/v glycerol, was added during the first primer annealing step at 37° C.

(ix) PCR in the Presence of Proline, Using Taq DNA Polymerase.

PCR was performed in 25 μl reaction mixture containing 3 ng of Halobacterium marismortui genomic DNA template, 0.12 nM of each 28-mer oligonucleotide primers 3 and 4 described in section (i) above, 0.5 units of Taq DNA polymerase, 200 μM of each dNTP in PCR buffer containing: 10 mM Tris-HCl (pH 8.8 at 25° C.), 50 mM KCl, 0.08% Nonidet P40. MgCl2 concentrations of 1.0 mM and 1.8 mM were used in the absence and in the presence of 1.0M L-proline, respectively. L-proline was added from 5.5 M stock solution adjusted to pH 8.8 at 25° C. Reaction mixtures were preheated for 3 min at their respective denaturation temperatures, except for reactions performed at Td 95° C., that were preheated for 3 min at 94° C. and then subjected to 35 thermal cycles as follows: (I) 30 sec incubation at 91–95° C., as indicated in each experiment (denaturation step); (ii) 90 sec incubation at 55° C. (primer annealing step); and (iii) 60 sec incubation at 72° C. (primer extension).

(x) PCR in the Presence of Proline, Using a Mixture of Klentaq1 and Pfu (or Vent) DNA Polymerases.

PCR was performed in 25 μl reaction mixture containing 250 ng of Halobacterium marismortui genomic DNA template, 0.12 nM of each 30-mer oligonucleotide primers 5 and 6 described in section (i) above, 0.3 μl of Klentaq1 and Pfu (or Vent) enzymes mixture, prepared as described (Barnes, 1994), 200 μM of each dNTP, in PCR buffer containing: 10 mM Tris-HCl (pH 8.3 at 25° C.) and 50 mM KCl. Mg(OAc)$_2$ concentrations of 1.0 mM and 14.5 mM were used in the absence and in the presence of 4.0M L-proline, respectively. L-proline was added from 5.5 M stock solution adjusted to pH 8.3 at 25° C. Reaction mixtures were preheated for 1 min at their respective denaturation temperatures, except for reactions performed at Td 95° C., that were preheated for 1 min at 94° C., and then subjected to 35 thermal cycles as follows: (I) 30 sec incubation at 72–95° C., as indicated in each experiment (denaturation step); (ii) 90 sec incubation at 37–55° C., as indicated in each experiment (primer annealing step); and (iii) 7 min incubation at 63–69° C., as indicated in each experiment (primer extension).

Example 1

DNA Melting in the Presence of THP(B)

The effect of different concentrations of THP(B) on the melting profile of calf thymus DNA (42% GC) was studied. Melting experiments were conducted as described in Materials and Methods, section (ii), in the absence or presence of 0.8M, 2M, 3M and 4M THP(B).

Figure 2:
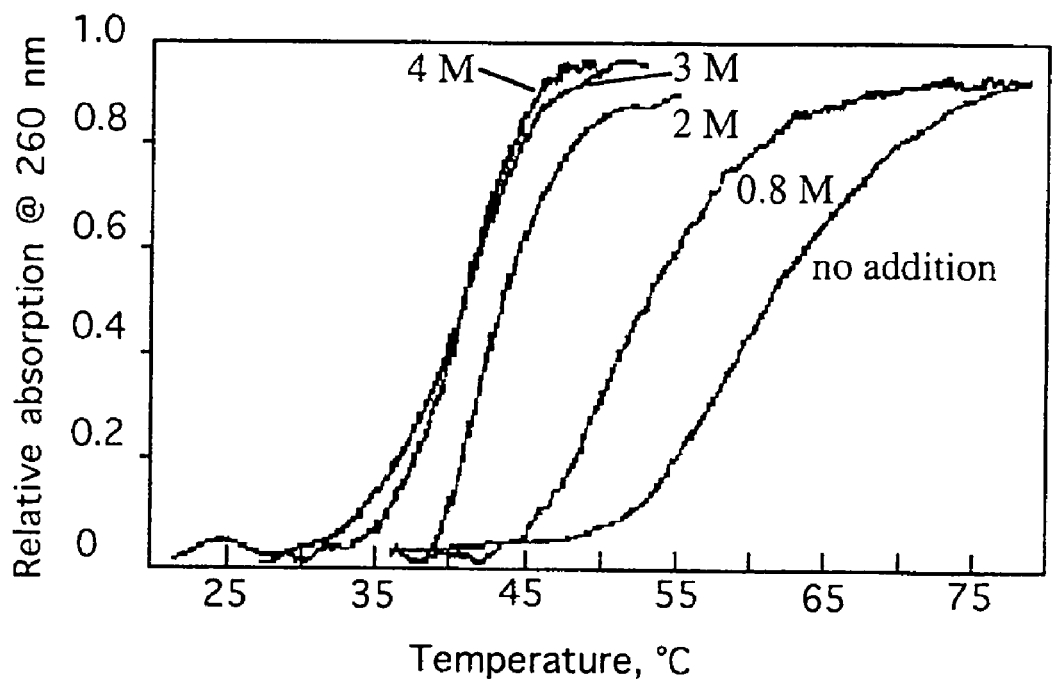
FIG. 2 depicts thermal transition of calf thymus DNA in the absence and presence of the indicated amounts of THP(B): 0.8M, 2M, 3M and 4M. DNA melting was performed as described in Materials and Methods, section (ii).

As shown in FIG. 2, the addition of THP(B) significantly lowered the DNA melting temperature and sharpened its transition profile. The DNA melting temperature in aqueous solution, 62° C., was lowered to 41° C. in the presence of 3 or 4M THP(B).

Figure 3:
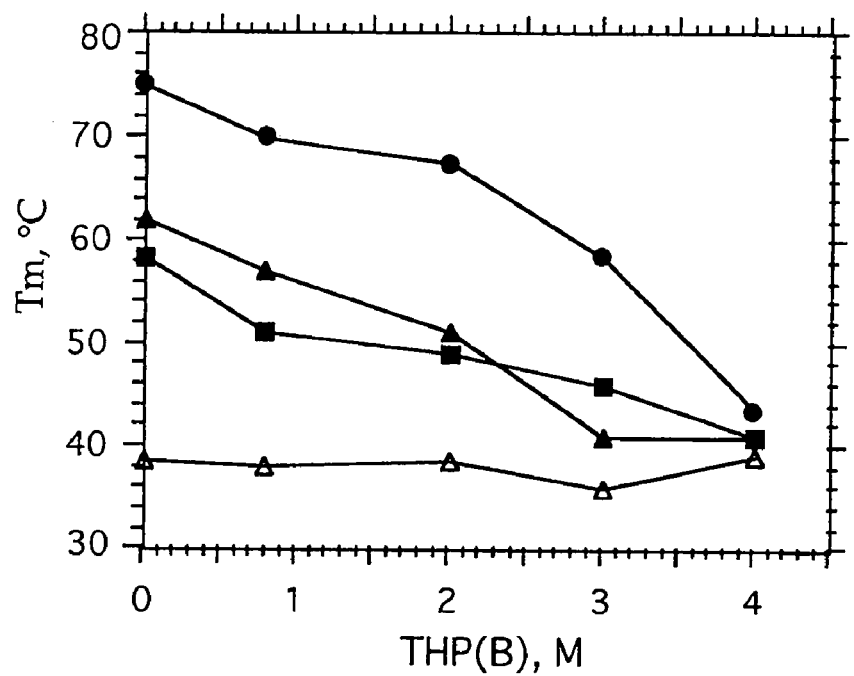
FIG. 3 depicts the variation of melting temperature (Tm) with THP(B) concentration for DNAs of varying base compositions. DNA melting was performed and Tms determined as described in Materials and Methods, section (ii), (filled triangles)—Calf thymus DNA; (filled circles)—*Micrococcus lysodeikticus* DNA; (filled squares)—*Clostridium perfringens* DNA; (open triangles)—poly(dA-dT).

The effect of THP(B) on DNA melting temperatures was examined on other DNAs with different base compositions, such as *Micrococcus lysodeikticus* and *Clostridium perfringens* DNAs (72% and 26% GC, respectively) and on the synthetic poly(dA-dT). As shown in FIG. 3, the melting temperatures (Tm) of the different DNAs decreased with the increase of THP(B) concentration in the incubation mixture. This effect is more pronounced for GC-rich DNAs. While the oligonucleotide poly(dA-dT) did not exhibit any change in the melting temperature in the presence of 1–4M THP(B), 3–4M THP(B) eliminated the base-pair composition dependence of DNA thermal melting. As shown in FIG. 3, in the presence of 4M THP(B), all DNAs with a wide range of GC content melt in a very narrow temperature range (40–43° C.), while in the absence of THP(B), the melting temperatures ranged from 39 to 75° C. This isostabilization effect by THP(B) may be explained as a result of greater destabilization of GC-rich than AT-rich DNAs.

Example 2

Short Oligonucleotides Melting in the Presence of THP(B)

Figure 4A:
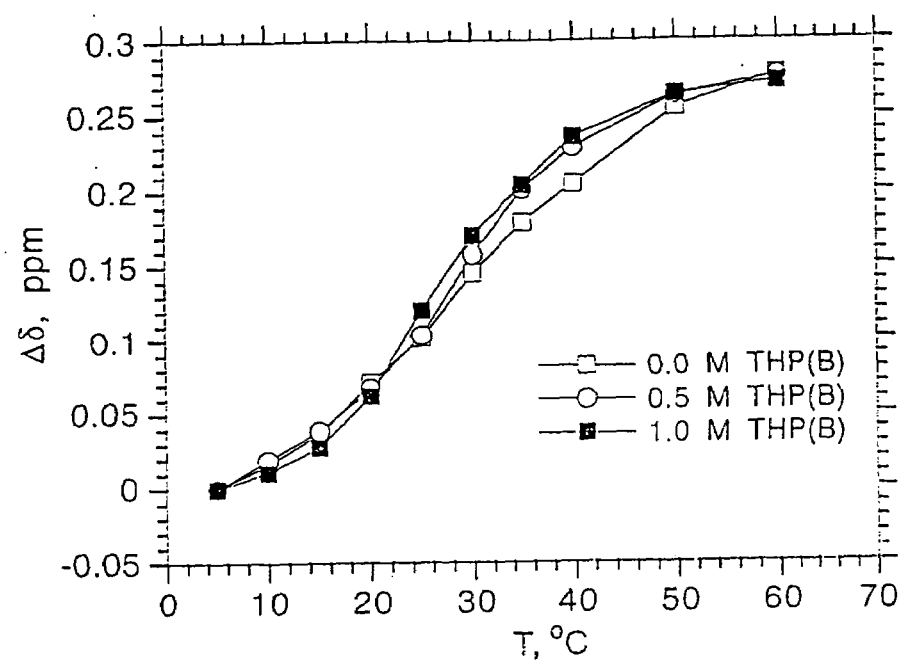
FIGS. 4A–B depict thermal transitions of the oligonucleotides [d(ATGCAT)]$_2$ (SEQ ID NO:1) and [d(GCTTAAGC)]$_2$ (SEQ ID NO:2), respectively. The chemical shifts of the C4H5 proton of [d(ATGCAT)]$_2$ (SEQ ID NO:1) and of the G1H8 proton of [d(GCTTAAGC)]$_2$ (SEQ ID NO:2) were measured as described in Materials and Methods section (iii), as a function of increasing temperatures in the absence (open squares) or presence of 0.5M (open circles) and 1M (filled squares) THP(B).
Figure 4B:
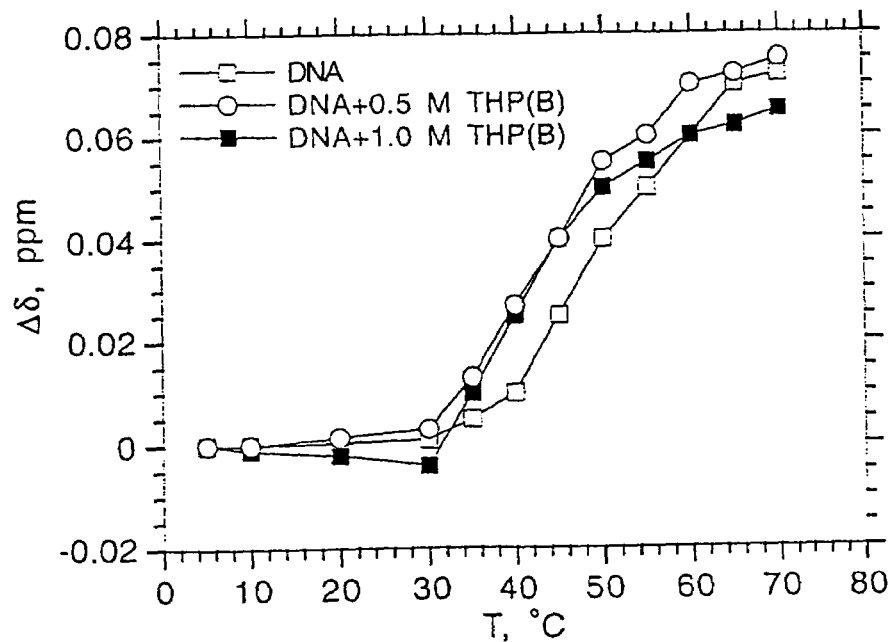

The thermal transitions of the short oligonucleotides [d(ATGCAT)]$_2$ (SEQ ID NO:1) (FIG. 4A) and [d(GCTTAAGC)]$_2$ (SEQ ID NO:2) (FIG. 4B) were studied in the absence (open squares) and presence of 0.5M (open circles) and 1.0M (filled squares) THP(B). NMR chemical shift changes of the C4H5 proton of [d(ATGCAT)]$_2$ (SEQ ID NO:1) and of the G1H8 proton of [d(GCTTAAGC)]$_2$ (SEQ ID NO:2) were measured as a function of increasing temperatures as described in Materials and Methods section (iii). The results of these experiments are depicted in FIGS. 4A–B and summarized in Table 1.

TABLE 1

| | | Tm° C. | | |
|---|---|---|---|---|
| | | DNA-THP (B) | | DNA-betaine |
| Oligonucleotide | DNA | 0.5M | 1.0M | 1.0M |
| [d(ATGCAT)]$_2$ (SEQ ID NO: 1) | 31.5 | 29.5 | 28.0 | 29.2 |
| [d(GCTTAAGC)]$_2$ (SEQ ID NO: 2) | 48.0 | 45.0 | 42.0 | — |

As shown in Table 1, the melting temperatures of [d(ATGCAT)]$_2$ (SEQ ID NO:1) and of [d(GCTTAAGC)]$_2$ (SEQ ID NO:2) decreased by 2° C. and by 3° C., respectively, in the presence of 0.5M THP(B), and by 3.5° C. and 6° C., respectively, in the presence of 1.0M THP(B). Data were compared to the melting temperature of [d(ATGCAT)]$_2$ (SEQ ID NO:1) in the presence of betaine. The decrease in Tm by betaine was only ~2° C. at 1.0M concentration, about two-fold higher concentration of betaine is needed for exerting the same Tm decline caused by THP(B).

Example 3

THP(B) and THP(A) Effects on Taq DNA Polymerase Stability at Elevated Temperatures The effects of THP(B) and THP(A) on the remaining activity of Taq DNA polymerase incubated at elevated temperatures for different periods of time were studied.

After 90 min incubation at 95° C., Taq DNA polymerase was only 30% active. The enzyme was remarkably stabilized upon addition of either THP(B) or THP(A). After incubation at 95° C. in the presence of 0.5M THP(B) or 0.5M THP(A), the half life of Taq polymerase was 70 min and 60–90 min, respectively, in comparison to the half life of 30–40 min observed in the absence of additive (not shown). Comparable protective effects were obtained when Taq DNA polymerase was incubated at 95° C. in the presence of a combination of THP(A) and THP(B) (results not shown). Thus, THP(B) and/or THP(A) present in the reaction mixture enable doubling PCR cycles without increased loss of enzyme activity.

Figure 5:
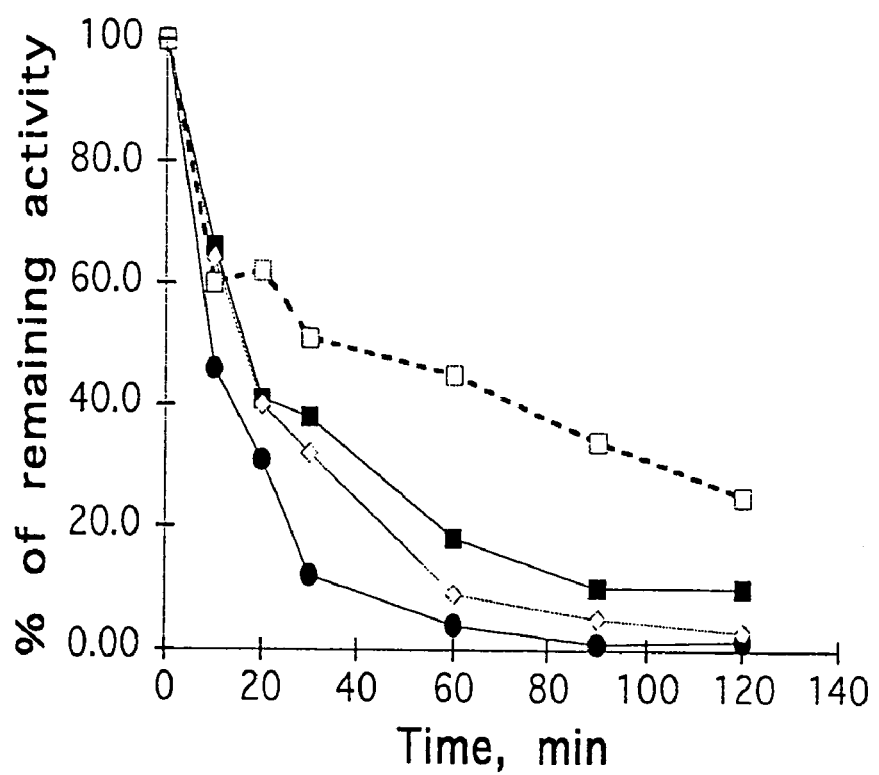
FIG. 5 depicts the time course of thermal inactivation of Taq DNA polymerase at 97° C. in the absence (filled circles) and presence of either 1M THP(B) (filled squares), 1M THP(A) (open squares) or 1M glycerol (open diamonds). The thermal inactivation was determined at different periods of time from Taq polymerase remaining activity measured as described in Materials and Methods, section (vi).

In FIG. 5 are shown results of similar experiments measuring the thermal inactivation of Taq polymerase at 97° C. in the absence (filled circles) or presence of 1M THP(B) (filled squares), 1M THP(A) (open squares) in comparison to 1M glycerol (open diamonds). The thermal inactivation of the enzyme at the elevated temperature 97° C. was, as expected, more rapid than the inactivation at 95° C.; almost a complete loss (>95%) of enzyme activity was observed following 60 min incubation at 97° C. with no additives. However, also the protective effects by THP(B) and THP(A) were more dramatic: the remaining Taq polymerase activities, following 30 min incubation at 97° C. were 40% and 50% in the presence of 1M THP(B) or THP(A), respectively, in comparison to 10% remaining activity in the absence of additives. As a result of 60 min incubation at 97° C., the remaining Taq polymerase activity in the absence of additive was 5%, whereas in the presence of 1M THP(B) or THP(A) the remaining activities were 20% and 45%, respectively. The results shown in FIG. 5 indicate that THP(A) is more effective than THP(B) or glycerol in stabilizing Taq DNA polymerase.

Example 4

PCR in the Presence of THP(B)

The combined effect of THP(B) on DNA melting temperatures and on Taq DNA polymerase activity and stability at elevated temperatures was followed under PCR conditions.

PCR reaction was performed by Taq DNA polymerase as described in Materials and Methods, section (vii), using as a template whole genomic DNA of *Halobacterium marismortui* (66.5% GC) and the 28-mer primers 1 and 2 described in section (i).

Figure 6:
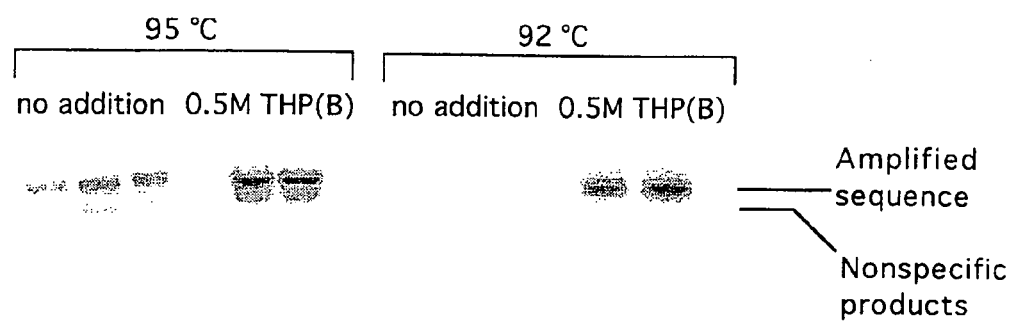
FIG. 6 depicts ethidium bromide staining of PCR-amplified DNA products run on 1.7% agarose gel. PCR was performed according to the procedure described in Materials and Methods, section (viii), for amplification of a 349 b.p. fragment (66.5% GC content) from *Halobacterium marismortui* genomic DNA template at two different denaturation temperatures (Td), 95° C. (left) and 92° C. (right), in the absence and in the presence of 0.5M THP(B), as indicated. Two or three repetitions of each experiment are shown.

In FIG. 6 are depicted the amplified DNA sequences produced by PCR performed at 95° C. and 92° C., in the absence and presence of 0.5M THP(B), respectively, showing that yield and specificity of the DNA amplification was improved by the presence of THP(B). At 92° C. amplified sequences were produced only in the presence of THP(B), but not in its absence.

Figure 7A:
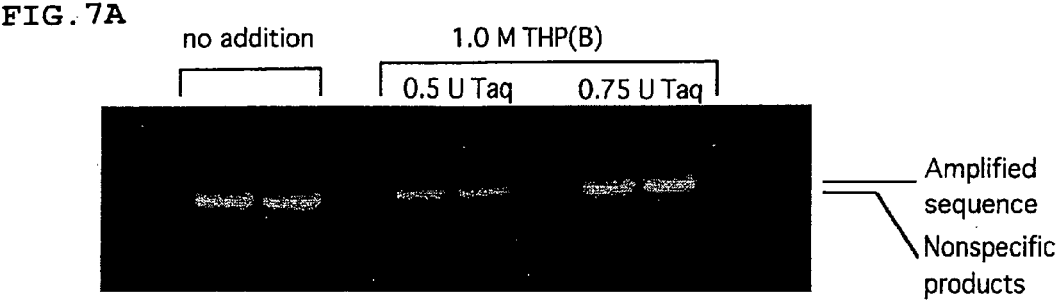
FIGS. 7A–C depict ethidium bromide staining of PCR-amplified DNA products run on 1.7% agarose gel. PCR was performed according to the procedure described in Materials and Methods, section (viii), for amplification of a 349 bp. fragment (66.5% GC content) from *Halobacterium marismortui* genomic DNA template at three different denaturation temperatures (Td): 95° C.
Figure 7B:
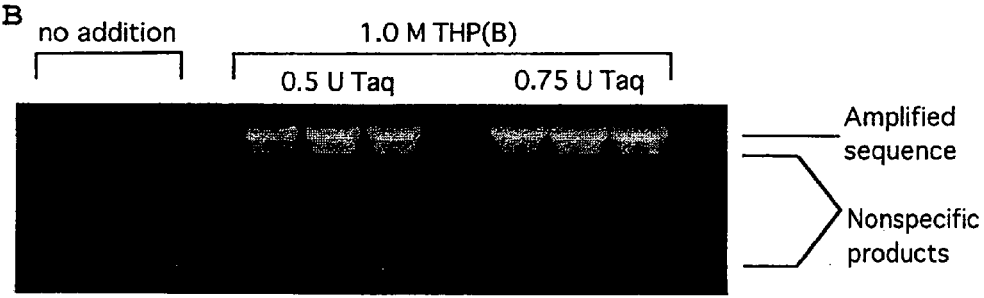
Figure 7C:
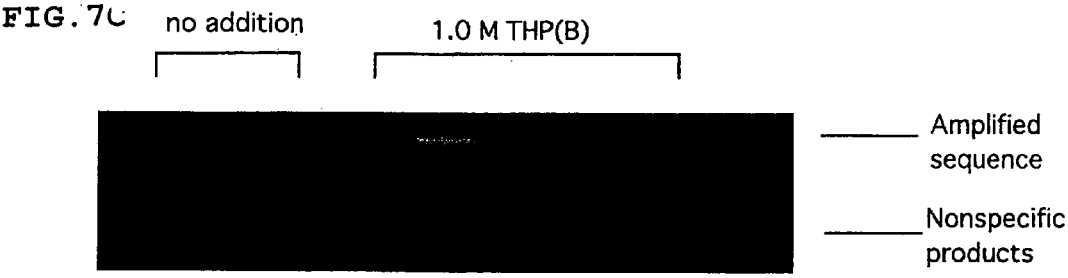

The effect of 1.0M THP(B) in the PCR buffer mixture is presented in FIGS. 7A–C. A "control" assay was performed at Td 95° C. in the absence and presence of 1.0M THP(B) with two concentrations of Taq DNA polymerase, 0.5 and 0.75 units in 25 μl PCR reaction mixture. The presence of 1.0M THP(B) improved PCR specific amplification at Td 95° C. (FIG. 7A). However, the most significant results were obtained when denaturation temperatures of the DNA were reduced from 95° C. to 90° C. (FIG. 7B) in the presence of 1.0M THP(B) (either with 0.5 or 0.75 units of Taq DNA polymerase in 25 μl reaction mixture). Under these conditions, specific amplified sequence was generated only in the presence of THP(B), while no trace of amplified DNA could be detected in the absence of this additive.

When Td was further lowered to 89° C. in the presence of 0.5 units Taq DNA polymerase in 25 μl reaction mixture, amplified DNA sequence was markedly lower, even in the presence of 1.0M THP(B) but no trace of amplified DNA was detected in the absence of THP(B) (FIG. 7C).

Example 5

DNA Melting in the Presence of Proline

The effect of different concentrations of proline on the melting profile of calf thymus DNA (42% GC) was studied. Melting experiments were conducted as described in Materials and Methods, section (ii), in the absence or presence of 2M, 3.5M 5M and 6.2M proline.

Figure 8A:
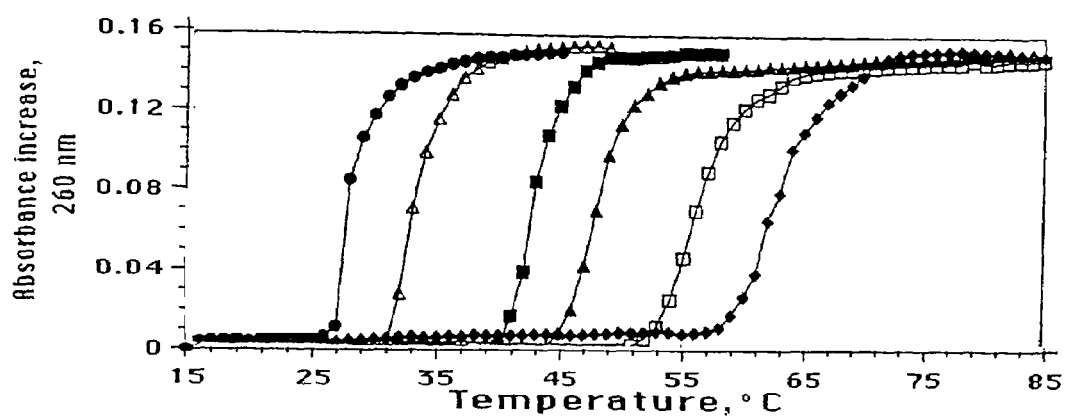
FIGS. 8A–8B depict thermal transition of calf thymus DNA (FIG. 8A) and other DNAs (FIG. 8B) in the presence and absence of proline. DNA melting was performed as described in Materials and Methods, section (ii).

As shown in FIG. 8A, the addition of proline significantly lowered the DNA melting temperature and sharpened its transition profile. The DNA melting temperature in aqueous solution, 62° C., was lowered to 27° C. in the presence of 6.2M proline.

Figure 8B:
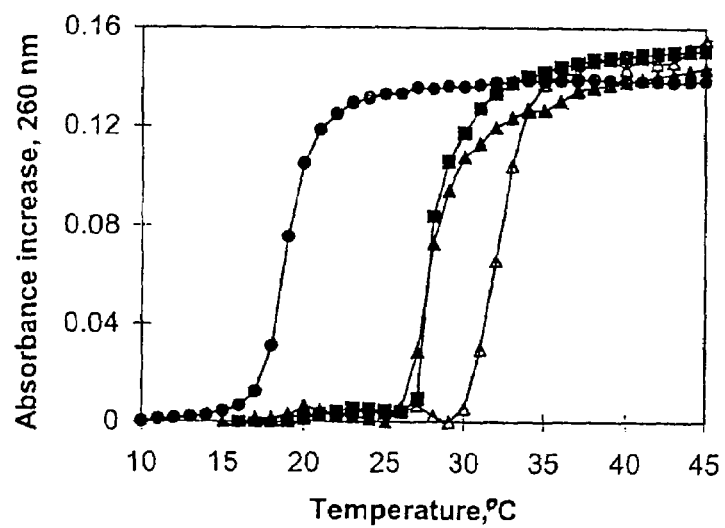

The effect of proline on DNA melting temperatures was examined on different DNAs with different base compositions, such as *Micrococcus lysodeikticus* and *Clostridium perfringens* DNAs (72% and 26% GC, respectively), calf thymus DNA (42% GC) and on the synthetic poly(dA-dT). As shown in FIG. 8B, the melting temperatures (Tm) of the different DNAs decreased in the presence of 6.2M proline concentration in the incubation mixture. The range of melting DNA with GC content of 72% is about 5° C. higher than that of GC content of 42% and 26%, while poly(dA-dT) melts about 15° C. lower.

Figure 9A:
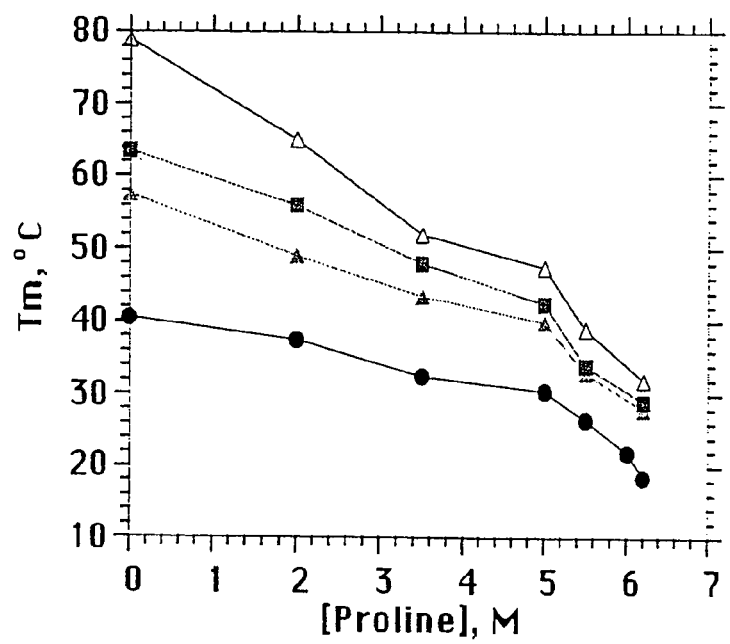
FIG. 9A depicts a variation of Tm with proline concentration for DNAs of varying base compositions. DNA melting was performed as described in Materials and Methods, section (ii), (filled squares)—calf thymus DNA; (open triangles)—*Micrococcus lysodeikticus* DNA; (filled triangles)—*Clostridium perfringens* DNA; (filled circles)—poly(dA-dT).

The effect of increasing concentration of proline as depicted in FIG. 9A on the four DNAs reveals that the effect was pronounced for GC-rich DNAs. While the oligonucleotide poly(dA-dT) did not exhibit any change in the melting temperature in the presence of 1–5M proline, a small effect occurred in the range of 5–6.2M proline. Proline at 6.2M almost eliminated the base-pair composition dependence of DNA thermal melting. As shown in FIG. 9A, in the presence of 6.2M proline all DNAs with a wide range of GC content melt in a very narrow temperature range (25–32° C.), while in the absence of proline the melting temperatures ranged from 38 to 78° C.

Figure 9B:
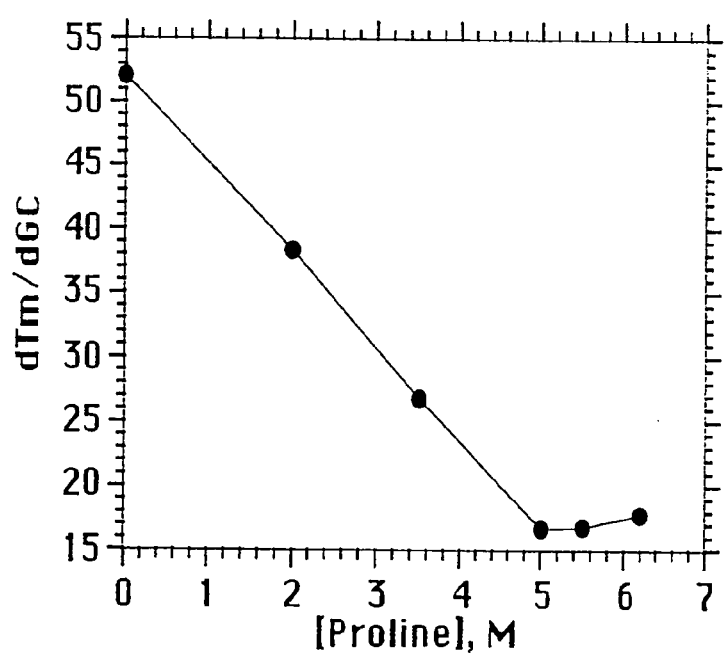
FIG. 9B depicts changes in dTm/dGC as a function of proline concentration.

FIG. 9B depicts changes in dTm/dGC as a function of proline concentration. A linear correlation is presented for proline concentration of up to 5M.

Example 6

Klenow Polymerase Activity in the Presence of Praline

To study the effect of 5.0M L-proline on the Klenow DNA polymerase activity, experiments were conducted as described in Materials and Methods, section (iv), in the presence of different concentrations of $MgCl_2$: 6.7 mM, 10.0 mM and 15.0 mM $MgCl_2$.

Figure 10:
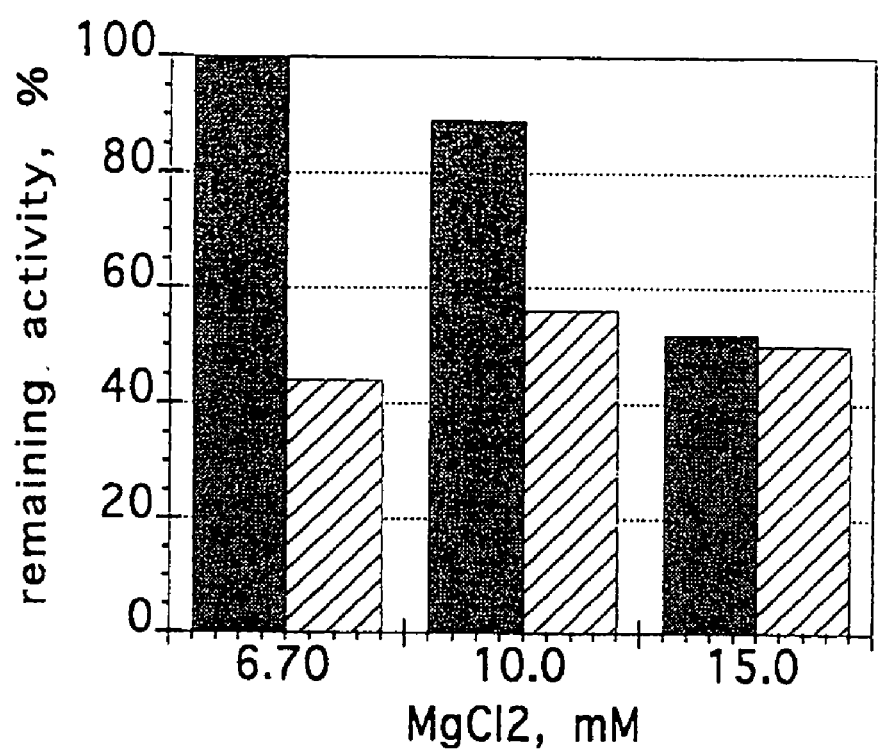
FIG. 10 depicts Klenow DNA polymerase activity at 37° C. in the absence (dark bars) and in the presence of 5.0M proline (hatched bars). The activity of Klenow DNA polymerase was measured at 6.7, 10 and 15 mM MgCl$_2$ as described in Materials and Methods, section (iv).

As shown in FIG. 10, L-proline only slightly decreased Klenow DNA polymerase activity. The activity of the enzyme remained high enough, particularly at 10.0 (hatched bar, middle) and 15.0 mM $MgCl_2$ (hatched bar, right).

Example 7

The Effect of 5.0M Proline on the Stability of Klenow DNA Polymerase at 65° C.

The remaining activity of Klenow DNA polymerase incubated at 65° C. in the presence of 5.0M proline, 5.0M glycerol or without any additives, was measured as described in Materials and Methods, section (vi). As shown in FIG. 11, Klenow DNA polymerase at 65° C. has a half-life of less than one minute with no additives (filled circles), 3 minutes in the presence of 5.0M glycerol (filled triangles) and 21 minutes in the presence of 5.0M proline (open diamonds).

Example 8

PCR in the Presence of Proline, Using Klenow DNA Polymerase

The combined effects of proline on Klenow DNA polymerase stability at elevated temperatures and on DNA denaturation temperature step, permitted a successful design of cycled PCR conditions for this enzyme. PCR was performed by Klenow DNA polymerase as described in Materials and Methods, section (viii).

PCR amplification of a 349 b.p. fragment (66.5% GC) of *Halobacterium marismortui* genomic DNA (from position 2546 to 2843) was performed in a 25 μl reaction mixture containing 100 ng of the DNA template, 0.12 nM of each 3-mer oligonucleotide primers 5 and 6 described in section (i) above, 0.9 mM of each dNTP, 10 mM Tris-HCl (pH 7.4 at 25° C.) and 15 mM of magnesium acetate. Tris-HCl buffer, template DNA, dNTP, primers and magnesium acetate were added to PCR microtubes from stock solutions, evaporated to dryness by speed-vacuum and dissolved in 22μl of a proline-glycerol solution, containing 5.5M of L-proline in a 12.5% w/v solution of glycerol in water.

Klenow polymerase (10 units/μl, storage buffer contains 50% w/v glycerol) and, in order to keep constant glycerol concentration in the PCR mixtures, aliquots of glycerol solution in water (50% w/v glycerol) were added during the first primer annealing step.

Figure 12:
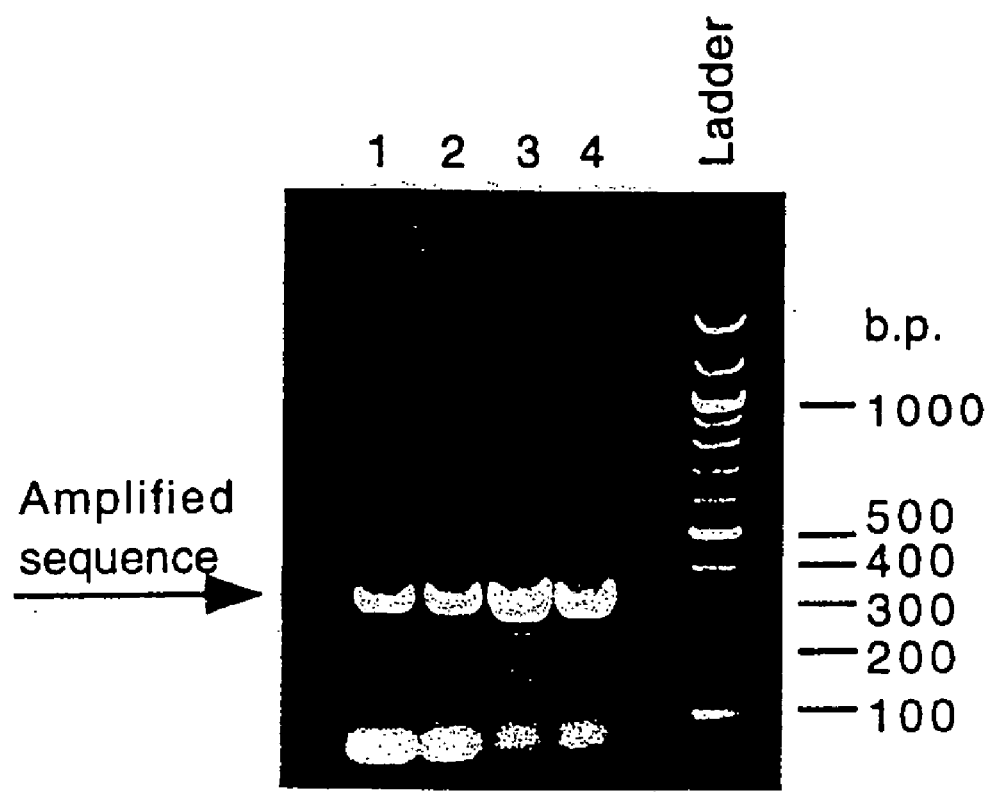
FIG. 12 depicts ethidium bromide staining of PCR-amplified DNA products ran on 2.0% agarose gel. PCR was performed according to the procedure described in Materials and Methods, section (ix), for amplification of a 349 b.p, fragment (66.5% GC) from *Halobacterium marismortui* genomic DNA, using 10 and 15 units of Klenow fragment of DNA polymerase I.

As shown in FIG. 12, in lanes 1. and 2. 1.0 μl of Klenow polymerase (10 units) and 2.0 μl of the glycerol solution were added, and in lanes 3. and 4. 1.5 μl of Klenow polymerase (15 units) and 1.5 μl of the glycerol were added. The final concentration of L-proline in all PCR mixtures was 4.85M and of glycerol was 17% w/v. All PCR reactions were run on a MJ Research PTC-100 machine equipped with a normal block (ramping rate is 1° C. per second). Reaction mixtures were preheated for 3 min at 75° C., and then subjected to 35 thermal cycles as follows: a) 20 sec incubation at 70° C.; b) 4 min incubation at 37° C. Reaction products were run on a 2% agarose gel and stained by ethidium bromide.

The results shown in FIG. 12 reveal that proline concentration in the range of 3–5.5M is sufficient to confer stability to Klenow DNA polymerase and to conduct a successful PCR protocol.

Example 9

PCR in the Presence of Proline, Using Taq DNA Polymerase

Figure 13:
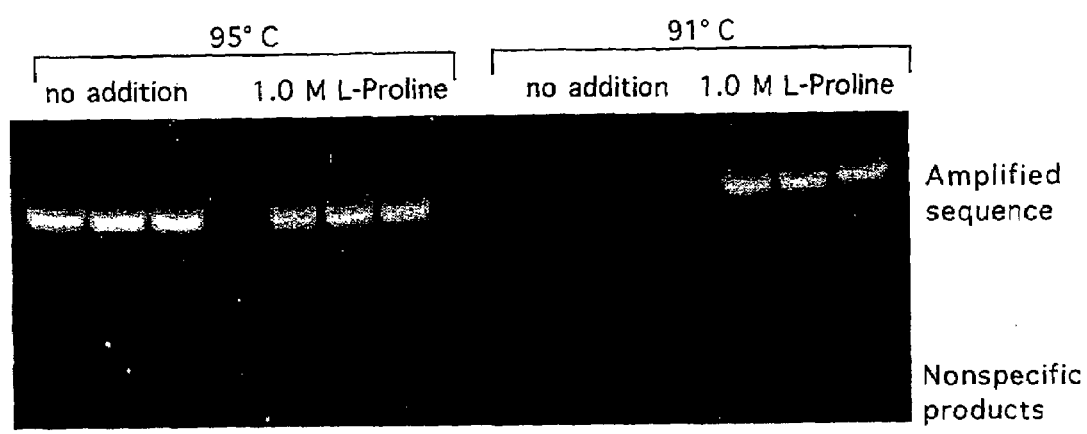
FIG. 13 depicts ethidium bromide staining of PCR-amplified DNA products run on 1.7% agarose gel. PCR was performed according to the procedure described in Materials and Methods, section (x), for amplification of a 349 b.p. fragment (66.5% GC) from *Halobacterium marismortui* genomic DNA template catalyzed by Taq DNA polymerase at two different denaturation temperatures (Td), at 95° C. and 91° C., in the absence and in the presence of 1.0M proline. Three repetitions of each experiment are shown.

FIG. 13 shows PCR, using Taq DNA polymerase, performed in the absence and in the presence of 1.0M proline, as described in Materials and Methods, section (ix). Addition of 1.0M proline to the reaction mixture did not impair PCR performance at denaturation temperature 95° C. and enabled successful PCR at decreased denaturation temperature, namely 91° C.

Example 10

PCR in the Presence of Proline, Using mixture of Klentaq1 and Pfu DNA Polymerases PCR was performed in the presence of 4.0M proline, using a mixture of Klentaq1 and Pfu DNA polymerases, as described in Materials and Methods, section (x). Reaction mixtures were preheated for 1 min at their respective denaturation temperatures (77° C. and 75° C.), and then subjected to 35 thermal cycles as follows: (i) 30 sec incubation at 77° C. or 75° C. (denaturation step); (ii) 90 sec incubation at 44° C. primer annealing step); and (iii) 7 min incubation at 65° C. (primer extension).

Figure 14:
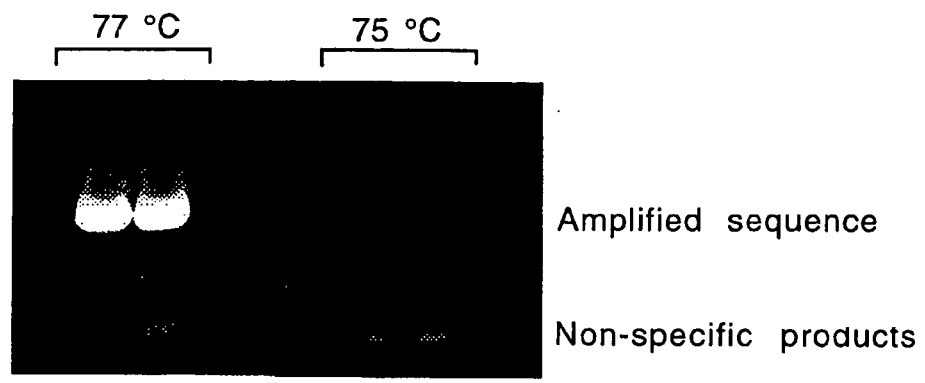
FIG. 14 depicts ethidium bromide staining of PCR-amplified DNA products run on 1.7% agarose gel. PCR was performed according to the procedure described in Materials and Methods, section (xi), for amplification of a 349 b.p. fragment (66.5% GC) from *Halobacterium marismortui* genomic DNA template catalyzed by KlenTaq1 DNA polymerase at two different denaturation temperatures (Td), at 77° C. and 75° C., in the presence of 4.0 M proline. Two repetitions of each experiment are shown.

As shown in FIG. 14, there is a clear correlation between the concentration of proline in the mixture and the minimal denaturation temperature. Thus, true for above mentioned conditions, 4.0M concentration of proline was enough for successful PCR at the 77° C. denaturation temperature, but not at 75° C.

REFERENCES

1. Barnes, W. M. (1994) PCR amplification of up to 35-kb DNA with high fidelity and high yield from λ bacteriophage templates, Proc. Natl. Acad. Sci 91, 916–2220.
2. Cheng, S., C. Fockler, W. M. Barnes and R. Higuchi (1994) Proc. Natl. Acad. Sci. U.S.A. 91, 5695–5699.
3. Corney, C. T., J. M. Jung and B. Budowle (1991) BioTechniques 10, 60–61.
4. Filichkin, S. A. and S. B. Gelvin (1992) BioTechniques 12, 828–830.
5. Galinski, E. A., H. P. Pfeifer and H. G. Truper (1985) Eur. J. Biochem. 149, 135–139.
6. Gelfand, D. H. and White (1989) in PCR Technology: Principles and Applications for DNA Amplification (Erlich, H. A., ed) pp. 17–22, Stockton Press, New York.
7. Han, J. et al. (1994) Nucleic Acids Research 22, 1735–1740.
8. Inbar, L. and A. Lapidot (1988a) J. Bacteriol. 170, 4055–4064.
9. Inbar, L. and A. Lapidot (1988b) J. Biol. Chem 263, 16014–16022.
10. Inbar, L., and A. Lapidot (1991) J. Bacteriol. 173, 7790–7801.
11. Inbar, L., F. Frolow and A. Lapidot (1993) Eur. J. of Biochem. 214, 897–906.
12. Kieleczawa, J., Dunn, J. J., and Studier, F. W. (1992) Science 258, 1787–1791.
13. Lapidot, A. Ben-Asher, E. and Eisenstein, M. (1995) FEBS Letters 367, 33–38.
14. Malin, G. M. and A. Lapidot (1996) J. Bacteriol. 178, 385–395.
15. Melchior, W. B., Von Hippel, P. H. Jr., and Von Hippel, P. H. (1973) Proc. Natl. Acad. Sci. USA. 70: 298–302
16. Mcpherson, M. J., P. Quirke and G. R. Taylor (1992) in PCR, A practical approach. (Mcpherson, M. J., Quirke P. and Taylor, G. R., Editors), IRL Press, Oxford University Press.
17. Mytelka, D. S. and M. J. Chamberlain (1996) Nucl. Acids Res. 24, 2774–2781.
18. Pomp, D. and J. F. Medrano (1991) BioTechniques 10, 58–59.
19. Rajendrakumar, S. V., Suryanarayana, T., and Reddy, A. R. (1997) FEBS Letters 410, 201–205.
20. Rees, W. A., T. D. Yager, J. Korte and P. H. Von Hippel (1993) Biochemistry 32, 137–144.
21. Varadaraj, K. and D. M. Skinner (1994) Gene 140, 1–5.

What is claimed is:

1. In a method for performing a cycled primer extension reaction using a non-thermostable polymerase, comprising:
   (i) contacting a template DNA comprising a target sequence of nucleotides with at least one primer oligonucleotide complementary to a nucleotide sequence at the 3'-end of said target sequence, under conditions allowing annealing of said primer to its complementary nucleotide sequence on said target sequence; and
   (ii) carrying out a polymerase-mediated extension of said primer on said target sequence of nucleotides, the improvement wherein the non-thermostable polymerase is stabilized and the operating temperatures are optimized for non-thermostable polymerase at temperatures where the non-thermostable polymerase would otherwise be inactivated, comprising:
conducting the cycled primer extension reaction in the presence of a sufficient concentration of proline to allow operating temperatures at which the non-thermostable polymerase is stabilized and optimized.

2. The method according to claim 1, wherein steps (i) and (ii) are repeated a plurality of time, and each step (i) is preceded by DNA thermal denaturation at a temperature suitable for separating both said template DNA into its strands and the polymerase-extended primer of step (ii) from its complementary target sequence of nucleotides, said temperature being a temperature in which the polymerase used in step (ii) is stable.

3. The method according to claim 1 for determining a nucleotide sequence of a target DNA, wherein in step (i) the target sequence of the template DNA is a sequence of nucleotides to be sequenced, and the polymerase-mediated extension of the primer in step (ii) is carried out in the presence of dATP, dCTP, dGTP and dTTP, and in the presence of a minute amount of either ddATP, ddCTP, ddGTP or ddTTP, prior to the determination of the nucleotide sequence of the target DNA.

4. The method according to claim 3, wherein dGTP is replaced by 7-deaza-dGTP.

5. In a method for determining a nucleotide sequence of a target DNA using a non-thermostable polymerase, comprising:
(i) heating a template DNA comprising a target sequence of nucleotides to be sequenced at a temperature suitable for separating said template DNA into its strands;
(ii) contacting said denatured template DNA of step (i) with a primer oligonucleotide complementary to a nucleotide sequence at the 3'-end of said target sequence of nucleotides under conditions allowing annealing of said primer to its complementary nucleotide sequence on the target sequence;
(iii) carrying out a polymerase-mediated extension of said primer of step (ii) in the presence of dATP, dCTP, dGTP and dTTP, of a minute amount of either ddATP, ddCTP, ddGTP or ddTTP;
(iv) repeating steps (i)–(iii) a plurality of times; and
(v) determining the nucleotide sequence of the target DNA,
the improvement wherein the non-thermostable polymerase is stabilized and the operating temperatures are optimized for non-thermostable protease at temperatures where the non-thermostable polymerase would otherwise be inactivated, comprising conducting the cycled primer extension reaction in the presence of a sufficient concentration of proline to allow operating temperatures at which the non-thermostable polymerase is stabilized and optimized.

6. The method according to claim 5, wherein dGTP is replaced by 7-deaza-dGTP.

7. The method according to claim 5 for amplifying a target sequence of nucleotides by polymerase chain reaction (PCR), wherein in step (i) the target sequence of the template DNA is a sequence of nucleotides to be amplified and the template DNA is contacted with two oligonucleotide primers complementary to the nucleotide sequences at the 3'-ends of said target sequence of nucleotides and its opposite strand; in step (ii) a polymerase-mediated extension of the annealed primers of step (i) is carried out; and steps (i)–(ii) are repeated a plurality of times, the last step being step (ii), thus generating multiple copies of the target sequence of nucleotides.

8. A method for amplifying a target sequence of nucleotides by polymerase chain reaction (PCR) using a non-thermostable polymerase, comprising:
(i) heating a template DNA comprising a target sequence of nucleotides to be amplified at a temperature suitable for separating said template DNA into its strands;
(ii) contacting the template DNA of step (i) with two oligonucleotide primers complementary to nucleotide sequences at the 3'-ends of said target sequence of nucleotides and its opposite strand, under conditions allowing annealing of said oligonucleotide primers to their complementary sequences on said target sequence of nucleotides and its opposite strand;
(iii) carrying out a polymerase-mediated extension of the annealed primers of step (ii); and
(iv) repeating steps (i)–(iii) a plurality of times, the last step being step (iii), thus generating multiple copies of the target sequence of nucleotides,
the improvement wherein the non-thermostable polymerase is stabilized and the operating temperatures are optimized for non-thermostable polymerase at temperatures where the non-thermostable polymerase would otherwise be inactivated, comprising:
conducting the cycled primer extension reaction in the presence of a sufficient concentration of proline to allow operating temperatures at which the non-thermostable polymerase is stabilized and optimized.

9. The method according to claim 1, wherein said template DNA is a GC-rich.

10. The method according to claim 8, wherein the non-thermostable DNA polymerase is selected from T7 DNA polymerase, T4 DNA polymerase, Klenow fragment of DNA polymerase I, reverse transcriptases, Bca DNA polymerase, Bst DNA polymerase, and mutants of these polymerases.

11. A kit for determining a nucleotide sequence of target DNA according to the method of claim 3, comprising in separate containers: (a) the reagents necessary for DNA sequencing, and (b) proline.

12. A kit for amplifying a target sequence of nucleotides according to the method of claim 7, comprising in separate containers: (a) the reagents necessary for a polymerase chain reaction, and (b) proline.

* * * * *